United States Patent [19]

Saint-Amand

[11] Patent Number: 4,877,036
[45] Date of Patent: Oct. 31, 1989

[54] SWAB TRANSPORT SYSTEM

[76] Inventor: Elmer F. Saint-Amand, 15740 Mill Meadow, Canyon Country, Calif. 91351

[21] Appl. No.: 276,639

[22] Filed: Nov. 28, 1988

Related U.S. Application Data

[62] Division of Ser. No. 107,408, Oct. 13, 1987, Pat. No. 4,813,432.

[51] Int. Cl.⁴ ............................................. A61B 10/00
[52] U.S. Cl. ..................... 128/749; 128/759; 206/438; 206/363; 206/569; 422/102; 435/296
[58] Field of Search ............... 128/749, 756, 757, 759; 215/DIG. 3; 422/58, 99, 101, 102; 435/294–296, 292; 206/569, 363, 438, 828

[56] References Cited

U.S. PATENT DOCUMENTS

| | | | |
|---|---|---|---|
| 3,918,435 | 11/1975 | Beall et al. | 128/759 |
| 3,954,564 | 5/1976 | Mennen | 435/295 |
| 4,353,868 | 10/1982 | Joslin | 435/295 |
| 4,409,988 | 10/1983 | Greenspan | 128/759 |
| 4,605,536 | 8/1986 | Kuhnert et al. | 422/58 |

Primary Examiner—Max Hindenburg
Assistant Examiner—Randy Citrin
Attorney, Agent, or Firm—James E. Brunton

[57] ABSTRACT

A swab transport apparatus for storing and transporting to a laboratory a swab containing a sample or specimen such as a micro organism sample. The uncontaminated swab is pre-packaged within a sterile swab storage chamber of the apparatus from which it can conveniently be removed for taking a sample. Disposed proximate the swab storage chamber and in communication therewith, is a squeeze bulb to which a suitable transport medium can be added either at time of manufacture of the device, or shortly prior to use. Following addition of the transport medium the squeeze bulb and the return of the contaminated swab to the apparatus, the squeeze bulb is squeezed to cause the transport medium to flow, preferably via a circuitous path, into the swab storage chamber. The apparatus can then be forwarded to the laboratory for testing with the swab safely immersed within the appropriate transport medium. In an alternate form of the apparatus, a second squeeze bulb is provided. This second squeeze bulb is in communication with the swab storage chamber and enables withdrawal therefrom of a sample of the transport medium which surrounds the contaminated swab. Where appropriate, the second squeeze bulb can be severed from the apparatus and forwarded to the laboratory for preliminary testing.

4 Claims, 6 Drawing Sheets

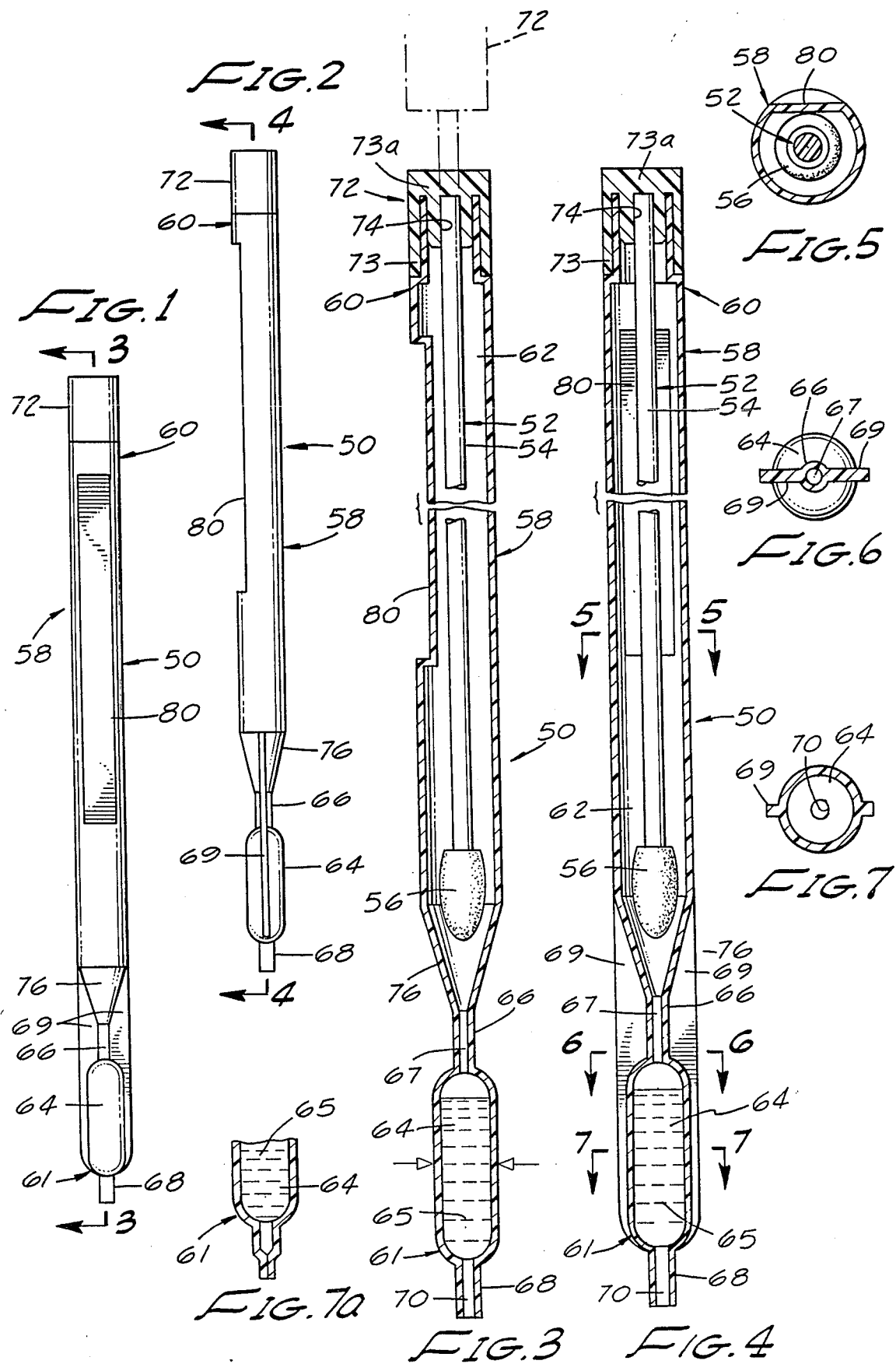

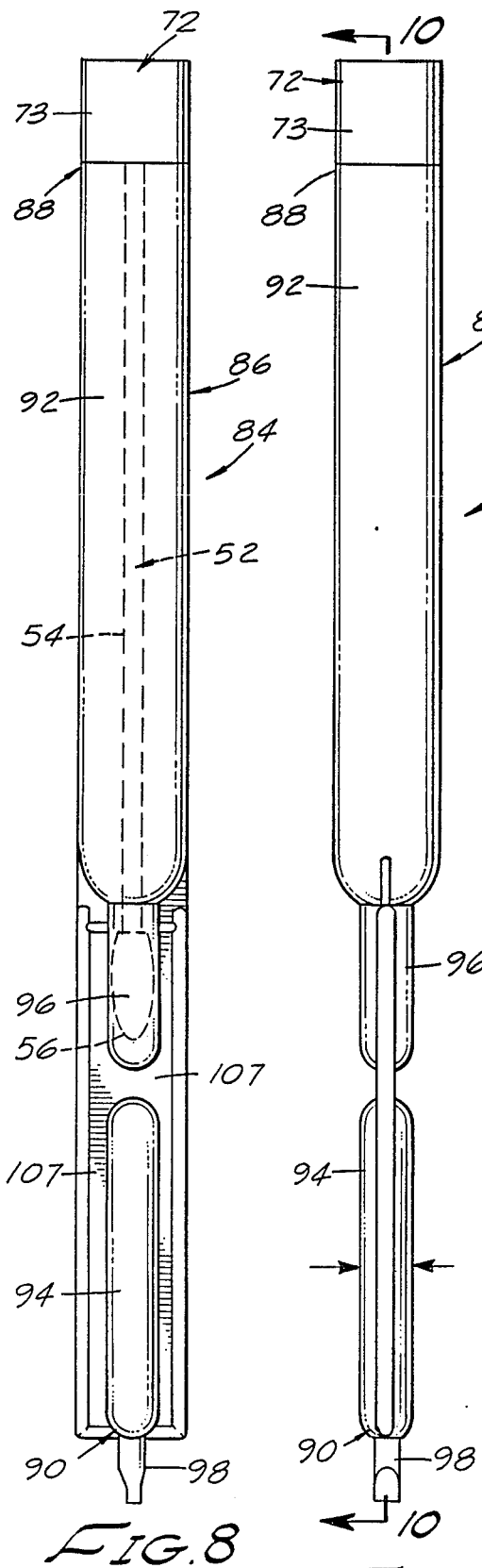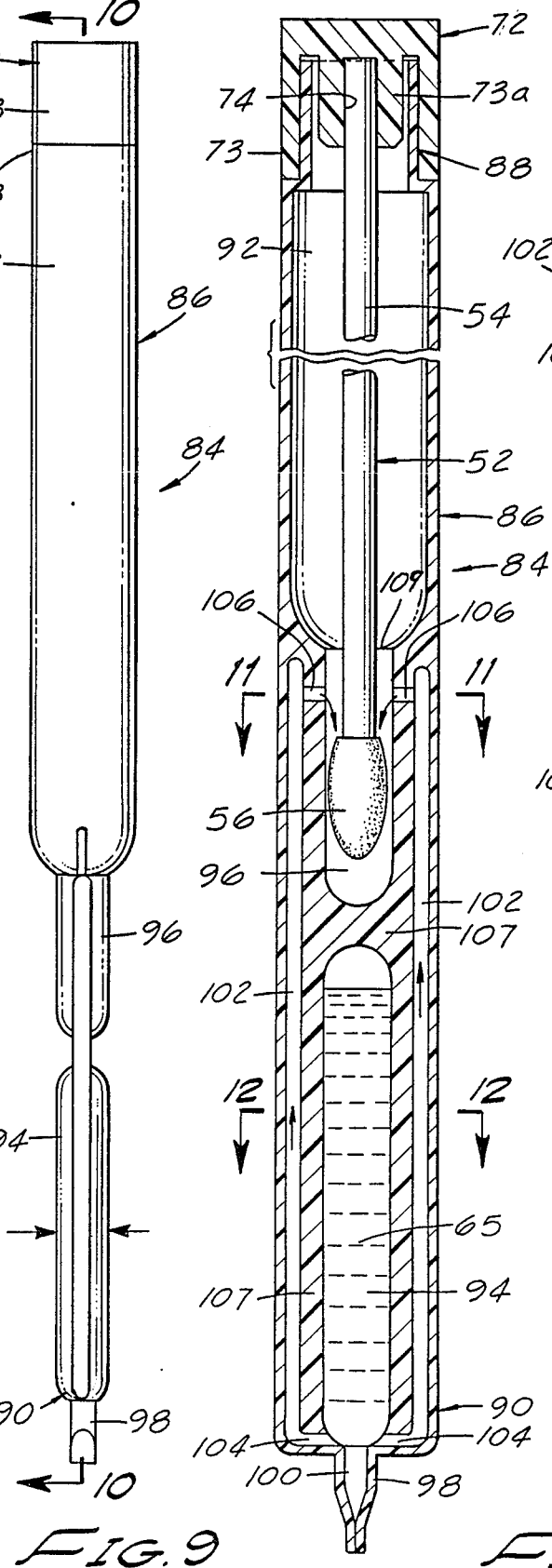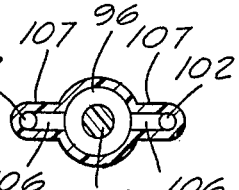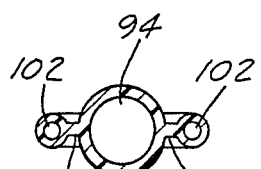

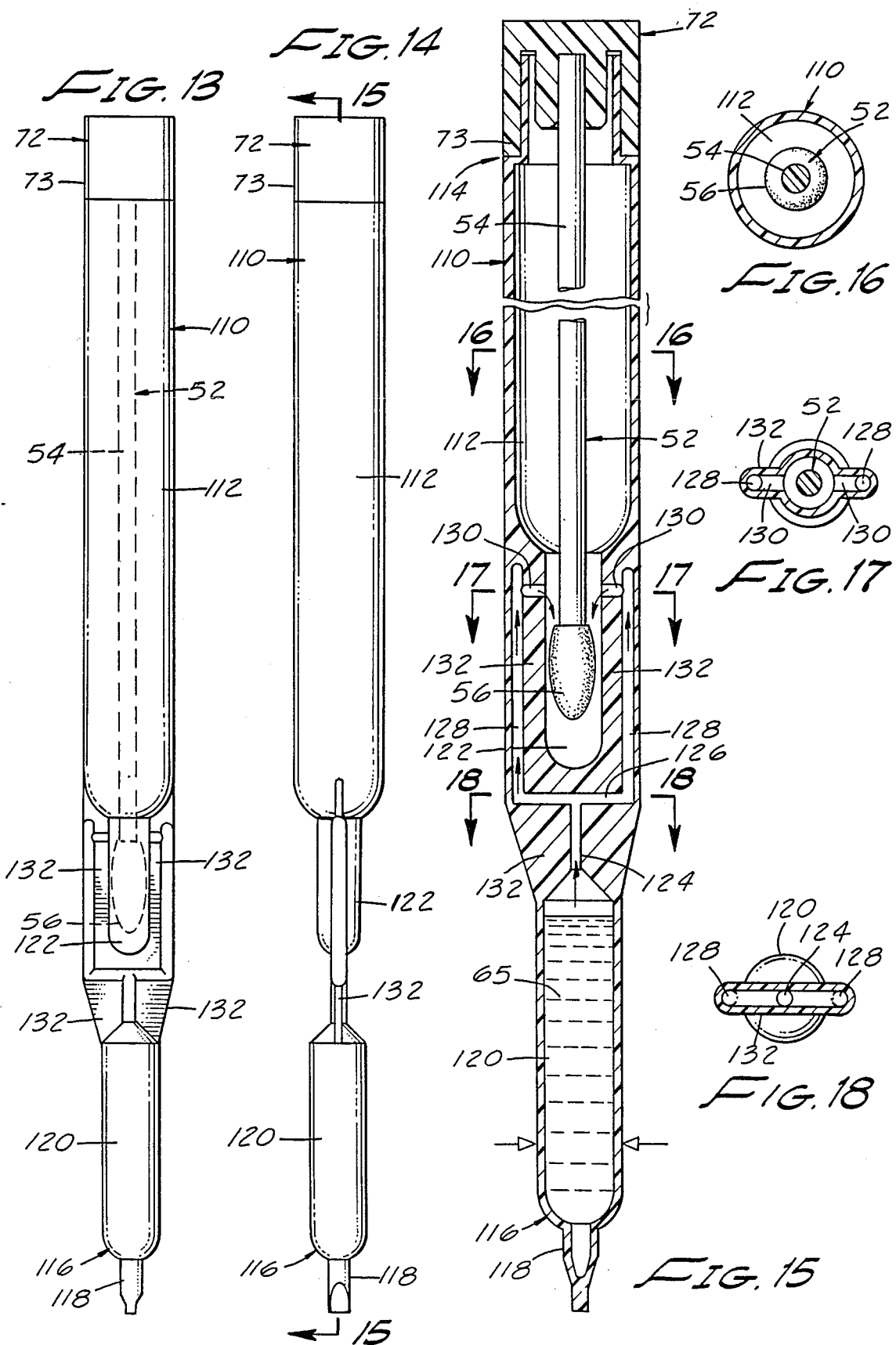

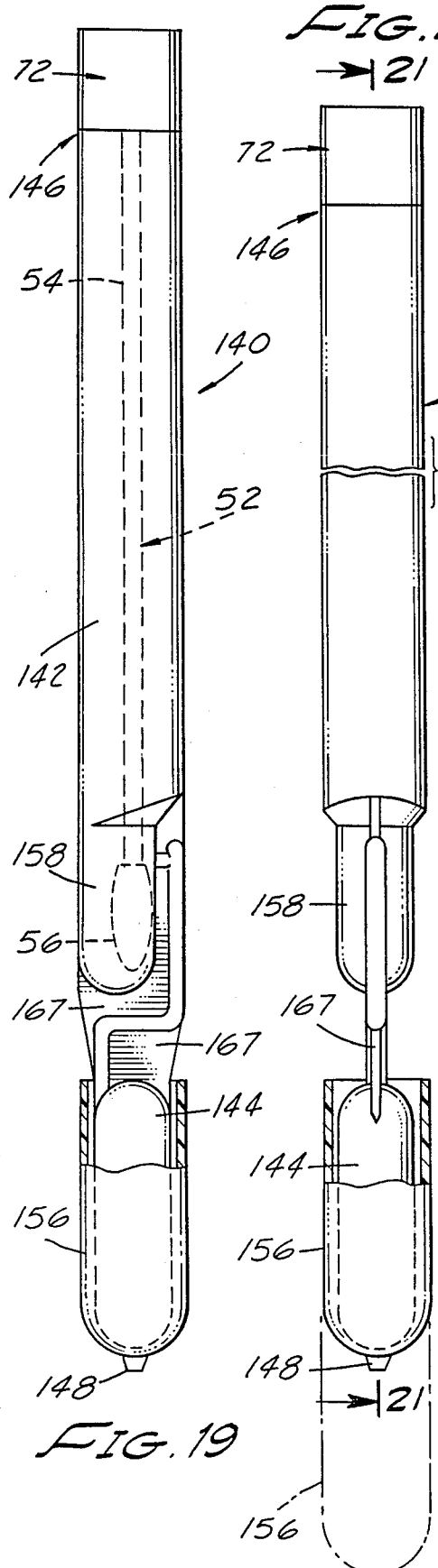
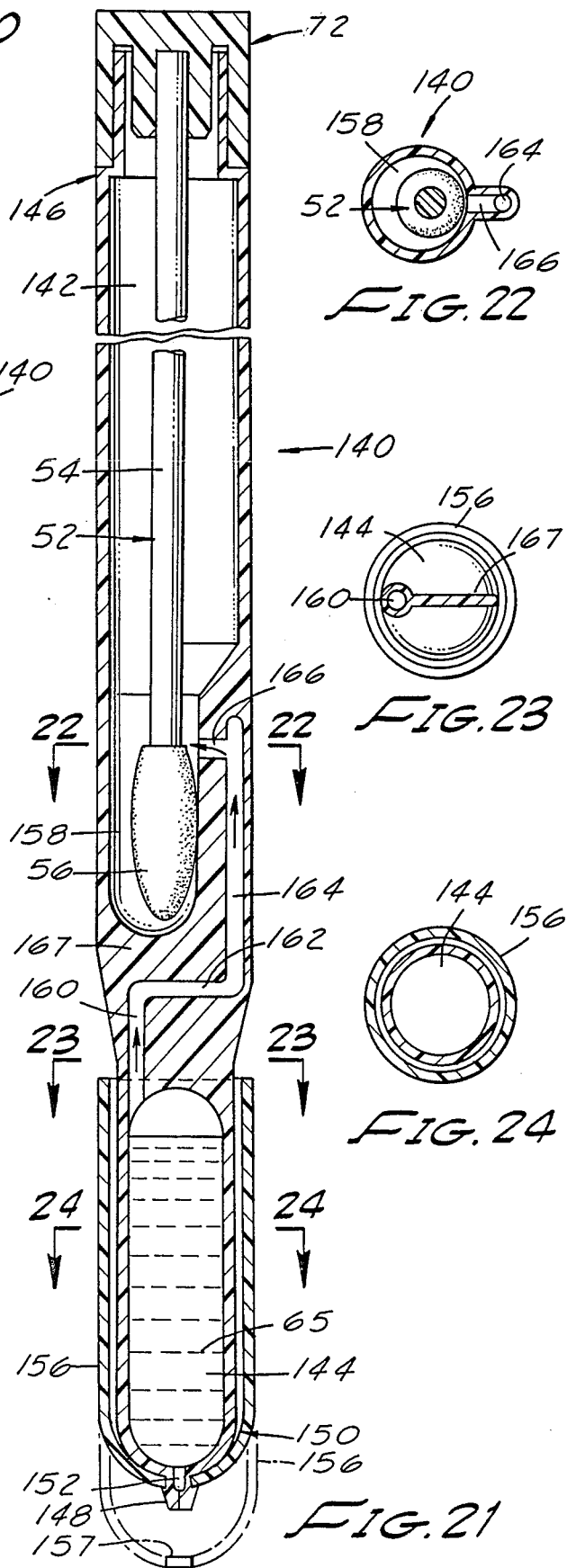
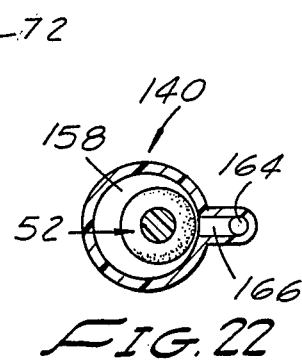
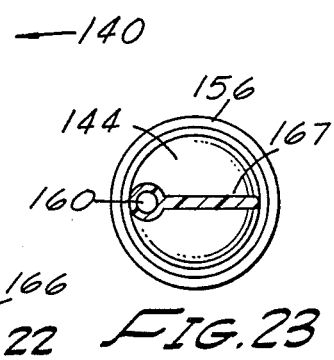
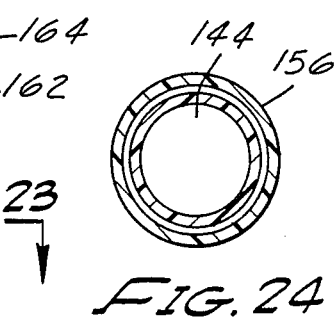
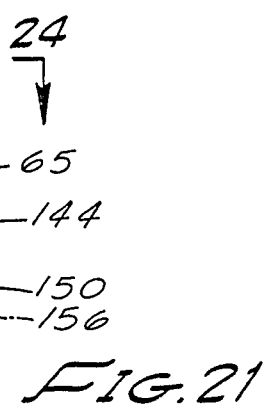

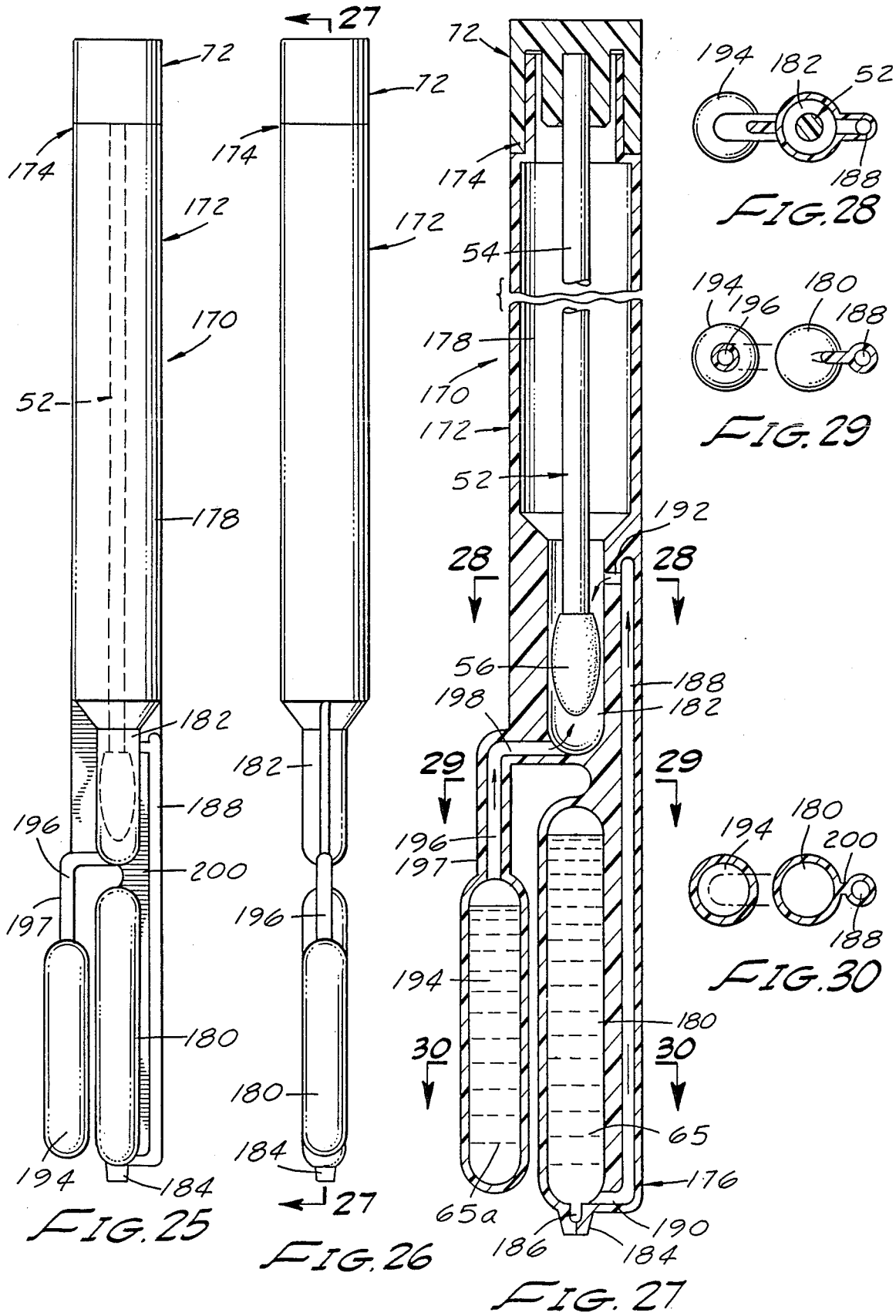

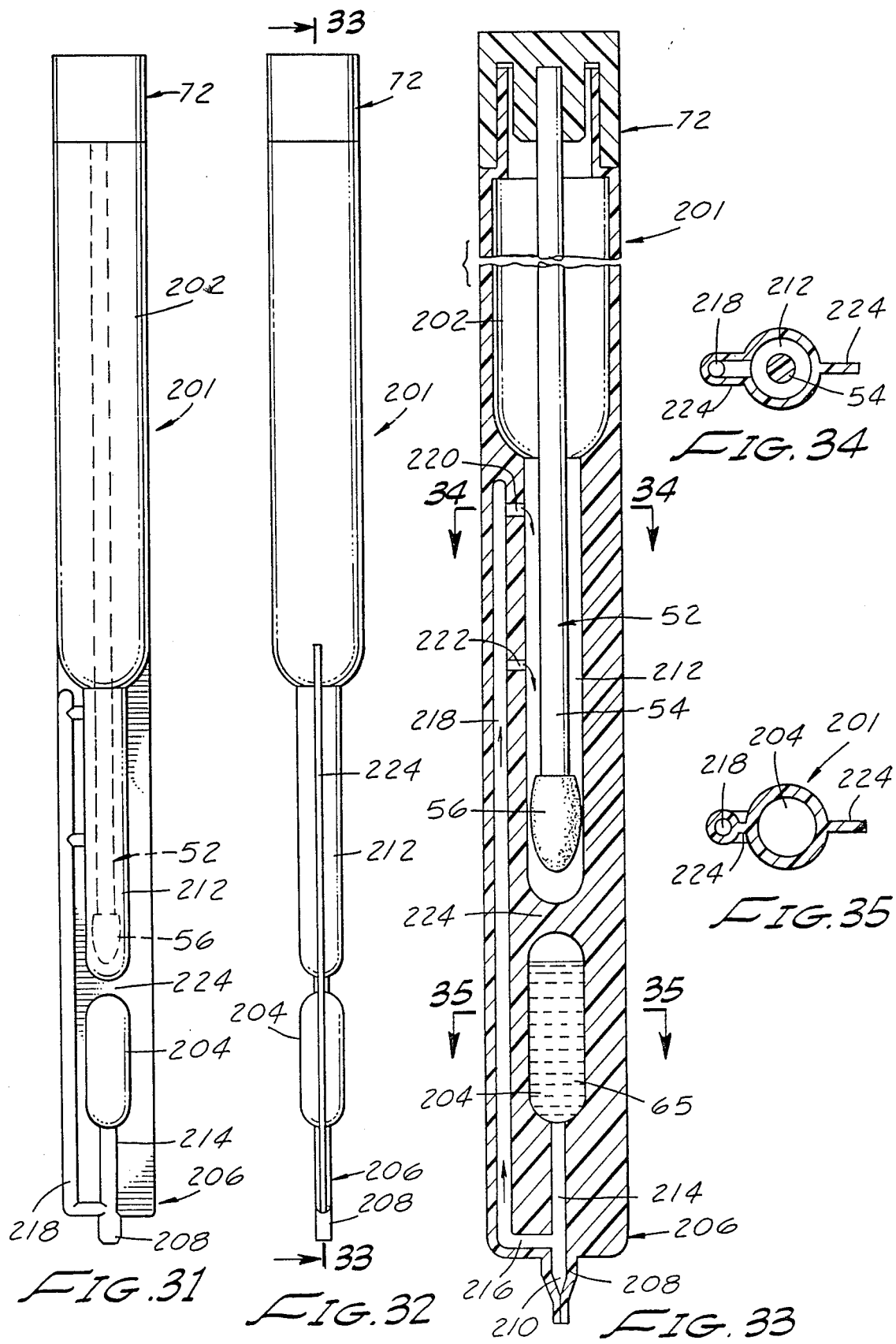

SWAB TRANSPORT SYSTEM

This Application is a Division of Copending Application Ser. No. 07/107,408 filed Oct. 13, 1987, now U.S. Pat. No. 4,813,432.

FIELD OF THE INVENTION

The present invention relates generally to a disposable swab transport apparatus. More particularly, the invention concerns an apparatus for obtaining a sample of organisms, such as bacteria, which may be present in or on various parts of the body and preserving the sample by immersing it within a selected transport medium during transport of the sample to a clinical laboratory for testing. The transport medium can be added to the apparatus at time of manufacture or, alternatively, can conveniently be added to the apparatus shortly prior to use.

DISCUSSION OF THE PRIOR ART

It is frequently necessary for a physician to obtain a sample of an organism from a patient. As a general rule, the physician removes a sterile swab from its supply package, contacts the area from which the specimen is to be taken and then forwards the swab to a laboratory for testing. Without the exercise of great care during transport, the specimen can become contaminated with foreign particles or organisms and the swab, itself can undesirably spread contamination on route to the laboratory. Further, unless the specimen is maintained in a viable state, such as by treatment of the swab with an appropriate preservative medium, an accurate analysis cannot be obtained.

In the past efforts have been made to provide a disposable swab container within which the transport medium is prepackaged. One such prior art apparatus consists of a two section tube having a swab in one section and a supply of transport medium in the other section. A slotted valve is provided between the two sections to permit the swab to be exposed to the transport medium. Another device consists of a flexible tube having a frangible ampoule in one end, absorbent material adjacent the ampoule and a swab disposed in contact with the absorbent material. In using this device a sample is taken with the swab, the swab is inserted into the flexible walled container and the area containing the ampoule is squeezed to break the ampoule. The medium contacts the absorbent material which then moistens the tip of the swab in contact with the absorbent material.

Still another prior art device provides a flexible walled swab enclosure and a closure cap carrying a hollow stemmed swab. A frangible, medium containing ampoule is mounted in the housing. With this device, after the sample is taken, the physician squeezes the housing to fracture the ampoule. The initial squeezing of the housing followed by repeated squeezing of the housing pumps the medium down the swab stem into contact with the absorbent material in the swab tip. This latter described device is more fully discussed in U.S. Pat. No. 3,918,435, issued to Beall et al. Other prior art apparatus for transporting swabs and specimens is described in U.S. Pat. Nos. 3,163,160, 3,282,114, 3,616,265 and 3,674,004.

In most, if not all, of the prior art devices the transport medium is pre-packaged within the apparatus, as sold. Accordingly, if different types of transport mediums are required for preserving the different specimens which are to be taken, different apparatus must be purchased and maintained in inventory. Another drawback of the prior art swab transport devices which carry the transport medium during transport and storage is the potential for leakage of the medium from the device and the potential for accidental exposure of the sterile swab to the transport medium prior to the specimen being taken. In either case, the often costly apparatus must be discarded.

The drawbacks of the prior art swab transport devices are uniquely overcome by the apparatus of the present invention which is designed to permit addition of an appropriate transport medium to the apparatus either at time of manufacture or immediately prior to using the apparatus. Further, the aparatus of the invention is uniquely constructed to positively prevent accidental premature exposure of the swab to the transport medium.

SUMMARY OF THE INVENTION

It is an object of the present invention to provide a novel disposable, blow molded swab transport apparatus having a flexible walled first chamber within which the swab is maintained in a sterile condition and a second chamber in communication with the first chamber which carries the selected transport medium.

Another object of the invention is to provide an apparatus of the aforementioned character, in which the transport medium is introduced into the swab storage chamber via a circuitous flow path thereby preventing accidental exposure of the swab to the transport medium as a result of handling and transport of the apparatus.

Still another object of the invention is to provide a swab transport apparatus as described in the preceding paragraphs in which a specimen of the transport fluid which has been exposed to the contaminated swab can be obtained and separately transported to the laboratory for testing.

A further object of the invention is to provide a swab transport apparatus which includes a swab; a blow molded container having a swab chamber and a transport medium chamber; and a closure cap all of which can be inexpensively manufactured and then assembled together into a highly compact subassembly which can be easily packaged, used, transported and stored.

Yet another object of the invention is to provide a swab transport apparatus of the class described in which the blow molded container is provided with one or more longitudinally extending flat surfaces which provide a writing surface for inscribing appropriate identification data directly on the device at the time a specimen is taken.

BRIEF DESCRIPTION OF THE DRAWINGS

FIG. 1 is a front view of one form of the swab transport apparatus of the present invention.

FIG. 2 is a side elevational view of the apparatus.

FIG. 3 is a cross-sectional view taken along lines 3—3 of FIG. 1.

FIG. 4 is a cross-sectional view taken along lines 4—4 of FIG. 2.

FIG. 5 is a cross-sectional view taken along lines 5—5 of FIG. 4.

FIG. 6 is a cross-sectional view taken along lines 6—3 of FIG. 4.

FIG. 7 is a cross-sectional view taken along lines 7—7 of FIG. 4.

FIG. 7a is a fragmentary view of one end of the apparatus shown in FIG. 3 illustrating the appearance of the device following sealing of the inlet fill tube.

FIG. 8 is a front view of another embodiment of the swab transport apparatus of the present invention.

FIG. 9 is a side elevational view of the apparatus of FIG. 8.

FIG. 10 is a cross-sectional view taken along lines 10—10 of FIG. 9.

FIG. 11 is a cross-sectional view taken along lines 11—11 of FIG. 10.

FIG. 12 is a cross-sectional view taken along lines 12—12 of FIG. 10.

FIG. 13 is a front view of still another form of swab transport apparatus of the present invention.

FIG. 14 is a side elevational view of the apparatus shown in FIG. 13.

FIG. 15 is a cross-sectional view taken along lines 15—15 of FIG. 14.

FIG. 16 is a cross-sectional view taken along lines 16—16 of FIG. 15.

FIG. 17 is a cross-sectional view taken along lines 17—17 of FIG. 15.

FIG. 18 is a cross-sectional view taken along lines 18—18 of FIG. 15.

FIG. 19 is a front view of yet another embodiment of the apparatus of the present invention.

FIG. 20 is a side elevational of the apparatus shown in FIG. 19.

FIG. 21 is a cross-sectional view taken along lines 21—21 of FIG. 20.

FIG. 22 is a cross-sectional view taken along lines 22—22 of FIG. 21.

FIG. 23 is a cross-sectional taken along lines 23—23 of FIG. 21.

FIG. 24 is a cross-sectional view taken along lines 24—24 of FIG. 21.

FIG. 25 is a front view of still another embodiment of the apparatus of the present invention.

FIG. 26 is a side elevational view of the apparatus shown in FIG. 25.

FIG. 27 is a cross-sectional view taken along lines 27—27 of FIG. 26.

FIG. 28 is a cross-sectional view taken along lines 28—28 of FIG. 27.

FIG. 29 is a cross-sectional view taken along lines 29—29 of FIG. 27.

FIG. 30 is a cross-sectional view taken along lines 30—30 of FIG. 27.

FIG. 31 is a front view of yet another embodiment of the apparatus of the present invention.

FIG. 32 is a side elevational of the apparatus shown in FIG. 31.

FIG. 33 is a cross-sectional view taken along lines 33—33 of FIG. 32.

FIG. 34 is a cross-sectional view taken along lines 34—34 of FIG. 33.

FIG. 35 is a cross-sectional taken along lines 35—35 of FIG. 33.

DESCRIPTION OF THE INVENTION

Referring to the drawings and particularly to FIGS. 1 through 7, one form of the swab transport apparatus of the present invention is thereshown and generally designated by the numeral 50. The apparatus of this form of the invention is used for transporting a swab 52 of the character having an elongated stem 54 and a bibulous swab material 56 carried proximate one end of the stem. As best seen by referring to FIGS. 3 and 4, the apparatus comprises an elongated plastic body 58 having resiliently deformable side walls and first and second end portions 60 and 61. Body 58 is open proximate its first or upper end 60 and includes a first elongated chamber 62 communicating with the open end for receiving the swab 52.

Body 58 also includes a second chamber 64 having resiliently deformable side walls for containing a fluid 65 therewithin. Second chamber 64 functions as a squeeze bulb, is axially aligned with chamber 62 and is longitudinally spaced therefrom. Disposed intermediate chambers 62 and 64 is a reduced diameter portion 66 which includes a communication path between first and second chambers 62 and 64 provided here as an axially extending passageway 67. Disposed proximate second end 61 of the plastic body is a tubular shaped segment 68 having a fluid passageway 70 therethrough for interconnecting second chamber 64 with atmosphere.

A removable first cover means is provided for sealably closing the open first end of body 58. This cover means is here provided as a plastic, cup-shaped member 72 having downwardly depending flexible, skirt like, side walls 73 adapted to sealably engage the side walls of tubular body 58 proximate the open upper end 60 thereof. Cap 72 includes a central portion 73a which is provided with an axially extending central bore 74 adapted to closely receive the upper end of elongated stem 54 of swab 52. With this construction, the swab can be removed from the apparatus by gripping the cap member 72 and simultaneously withdrawing the cap and the swab from the body portion 58 in the manner indicated by the phantom lines in FIG. 3. In this way, the sample can be taken without the physician touching any part of the swab itself. After the specimen has been taken, the swab can be reinserted into body 58, once again by handling only cap 72. A downward pressure exerted on cap 72 will cause the skirt, or wall portions, 73 to be received over and closely seal about the walls proximate the open first end 60 of the plastic body 58.

In the embodiment of the invention shown in FIGS. 3 and 4, it can be seen that body 58 further includes a generally frustoconical shape transition portion 76 disposed intermediate first chamber 62 and reduced diameter portion 66. The lower end of swab portion 56 is partially receivable within this transition portion when cap 72 is fully seated.

In using the apparatus illustrated in FIGS. 1 through 7, a fluid, such as a transport medium 65 can be added to chamber 64 at the time of manufacture via the open end of body 58 or through use of a syringe assembly with a needle adapted to penetrate the side walls of chamber 64. Alternatively, the transport medium 65 can be drawn into chamber 64 at any time prior to use by inserting tubular segment 68 into a vial containing the fluid, squeezing the flexible walls of chamber 64 and then releasing them to cause the fluid 65 to be drawn into chamber 64 in the manner shown in FIGS. 3 and 4. Once the transport medium most appropriate for use in connection with preserving the culture to be taken using the swab 52 is added to chamber 64, tubular segment 68 can be crimped and heat sealed in the manner shown in FIG. 7a. This heat sealing step can be accomplished in various ways understood by those skilled in the art and effectively closes off passageway 70 thereby preventing fluid flow through the passageway to the exterior of the apparatus.

After the specimen has been taken by the physician an the swab re-inserted into the apparatus in the manner shown in FIGS. 3 and 4 and with the tube segment 68 sealed in the manner shown in FIG. 7a, squeezing the yieldable side walls of chamber 64 will cause the transport fluid to be injected into the bottom portion of first chamber 62 via passageway 67. Chamber 64 is of a volume such that when the fluid is transferred from chamber 64 into chamber 62, the fluid will substantially encapsulate the bibulous swab material 56 carried by the swab. With the fluid transport medium saturating the bibulous swab material, the entire apparatus can be safely transported to the clinical laboratory for testing.

The ability to add the transfer medium to chamber 64 of the apparatus of the invention as depicted in FIGS. 1 through 7 via tubular segment 68 is particularly important when the selected transfer medium comprises a viscous liquid such as a gel. When such a medium is used it is virtually impossible to add the medium to chamber 64 via the open upper end 58.

Another useful feature of the apparatus of the invention shown in FIGS. 1 through 7 comprises the provision of a flat portion, or surface, 80 on the body portion 58. As best seen by referring to FIGS. 1, 2 and 5, portion 80 provides a convenient, smooth writing surface for inscribing thereupon appropriate identification data regarding the specimen taken and carried by the swab 52.

As indicated in the FIGS. 5, 6 and 7, plastic body portion 58 of the apparatus is substantially circular in crosssection at any point. As best seen in FIG. 6, reduced diameter portion 66 of the apparatus is reinforced through the provision of transversely spaced, longitudinally extending web portions 69.

Turning now to FIGS. 8 through 12, another form of the transport apparatus of the present invention is there shown and generally designated by the numeral 84. The apparatus of this form of the invention is used for transporting an identically configured swab 52 of the character previously described having an elongated stem 54 and a bibulous swab material 56 carried proximate one end of the stem. As best seen by referring to FIG. 10, the apparatus comprises an elongated plastic body 86 having yieldably deformable sidewalls and first and second end portions 88 and 90. Body 86 is open proximate its first or upper end 88 and includes the first elongated longitudinally extending chamber 92, communicating with the open end for receiving the swab 52.

Body 86 also includes a second chamber 94 having yieldable sidewalls for containing a fluid 65 therewithin. As best seen by referring to FIG. 9, second chamber 94 functions as a squeeze bulb, is axially aligned with chamber 92 and is longitudinally spaced therefrom. Deposed intermediate chambers 92 and 94, is a reduced diameter portion shown here as an intermediate chamber 96. Chamber 96 has flexible side walls and is in communication with chambers 92 and 94 via uniquely arranged fluid passageways presently to be described.

Disposed proximate second end 90 of the plastic body is a tubular shaped segment 98 having a passage way 100 therethrough for interconnecting second chamber 94 with atmosphere. In the drawings illustrating this second embodiment of the invention, tubular segment 98 is shown in a crimped or sealed configuration. In using the apparatus, chamber 94 is filled with an appropriate transfer medium prior to the sealing step by placing tubular segment 98 into a reservoir of the selected transport medium and then squeezing squeeze bulb or chamber 94 to draw the transport fluid into chamber 94. Once the transport fluid has been drawn into the apparatus, tubular segment 98 is sealed in the manner shown in the drawings. It is to be understood that, instead of sealing the tubular segment 98, as by heat sealing, segment 98 can be sealed using any type of suitable mechanical clamping device.

A removable first cover means having a configuration identical to that previously described is also provided for use in connection with the apparatus of the present form of the invention. This cover means, like that of the previously described embodiment of the invention, comprises a plastic cupshaped member 72 having downwardly depending flexible sidewalls 73 adapted to sealably engage the sidewalls of tubular body 86 proximate the open upper end 88 thereof. Cap 72 includes the central portion 73 which is provided with an axially extending central bore 74 adapted to closely receive the upper end of the elongated stem 54 of the swab 52. With the construction thus described, the swab can be removed, the specimen taken and the swab reinserted in the manner described in connection with the previous embodiment of the invention.

An important feature of the apparatus of the invention shown in FIG. 10 resides in the provision of a circuitous fluid flow path interconnecting intermediate chamber 96 with chamber 94. In the present embodiment of the invention this circuitous fluid flow path comprises transversely spaced, longitudinally extending fluid passageways 102 disposed on opposite sides of chambers 96 and 94 (FIG. 10). Proximate the lower extremities of passageways 102 are perpendicularly extending legs or passageways 104 which communicate with the lower extremity of chamber 94. Provided proximate the upper extremities of passageways 102, are vertically extending legs or short passageways 106 which communicate with chamber 96 proximate the upper end thereof. As indicated in FIG. 10, chamber 96 communicates with chamber 92 via a centrally disposed axially extending opening 109. With this arrangement, when swab assembly 52 is in position within the apparatus, bibulous portion 56 of the swab is received within chamber 96 and is positioned at a location below the transversally extending passageways 106.

In using the apparatus illustrated in FIG. 8 through 12 a fluid such as transport medium 65, if not added at time of manufacture, is drawn into chamber 94 in the manner previous described. Once the transport medium most appropriate for use in connection with preserving the culture to be taken is in place within chamber 94, tubular segment 98 is crimped and heat-sealed as depicted in the drawings. After the specimen has been taken by the physician and the swab is reinserted into the apparatus, squeezing the yieldable sidewalls of chamber 94 will cause the fluid within chamber 94 to be forced through fluid passageways 104 and 102 in the direction shown by the arrows in FIG. 10. The fluid will enter chamber 96 via transversely extending legs portions 106 and will saturate the bibulous portion 56 of the swab. It is to be understood that chamber 94 is of a volume sufficiently large so that the transport medium contained therein can be injected into chamber 96 to substantially fill the chamber so as to completely saturate the bibulous portion 56 of the swab during the time the apparatus is being transported to the laboratory for testing.

As indicated in FIGS. 11 and 12, chambers 94 and 96 are substantially circular in cross section with longitudinally extending passageways 102 being spaced apart from the axially centerline of the chamber and being carried within transversely extending weblike plastic portions 107 (FIGS. 8 and 10).

As was the case with the earlier described embodiment of the invention, body portion 86 along with tubular segment 98 is integrally formed by means of a blow molding process using a suitable blow-moldable plastic material selected from the olefin group.

Turning now to FIGS. 13 through 18, still another embodiment of the apparatus of the invention is there shown. Many portions of the apparatus of this form of the invention are identical to those previously described and the same reference numbers are used to identify components of like construction. For example, as indicated in FIG. 15, the cap portion 72 and the swab assembly 52 are of identical construction to that previously described herein save for the fact that swab 52 is provided with a slightly shorter stem and cap 72 is of a slightly larger diameter so as to sealably engage with the sidewalls of the body portion 110 which also is of a slightly larger diameter than the body portion of the transfer apparatus previously described.

The apparatus of this further form of the invention includes a longitudinally extending chamber 112 which is in communication with the upper open end portion 114 of body portion 110. Formed proximate the lower portion 116 of the body portion, is a tubular shaped segment 118 which is used to draw an appropriate transport fluid into a second chamber 120 of this embodiment of the invention. The tubular segment is then sealed in the manner shown in the drawing. The sidewalls of chambers 112 and 120 are yieldably deformable and function as squeeze bulbs.

Disposed intermediate chambers 112 and 120 is a reduced diameter portion including a third chamber comprising squeezably deformable bulb 122. As best seen in FIG. 15, in this form of the invention, chambers 112, 120 and 122 are all axially aligned and are in communication with one another via uniquely arranged fluid passageways of a character presently to be described.

Once again, an important aspect of the apparatus of this later form of the invention resides in the provision of a circuitous fluid flow path between chambers 120 and 122. This circuitous flow path prevents the inadvertent premature transfer of the fluid medium 65 from chamber 120 into the swab enclosing intermediate chamber 122 as might occur during handling or vibration of the apparatus.

As indicated in FIG. 15, the fluid flow path of the device this embodiment of the invention comprises an axially aligned fluid passageway 124 one end of which communicates with chamber 120 and the other end of which intersects a transversely extending passageway 126. At either end of passageway 126 there is provided longitudinally extending passageways 128 which are located on opposite sides of squeeze bulb 122. Longitudinally extending passageways 128 communicate proximate their upper ends with transversely extending passageway segments 130 which, in turn, communicate with chamber or squeeze bulb 122 proximate the upper end thereof.

In using this latest described form of the apparatus, a fluid such as transport medium 65 is prepackaged with the device, or is drawn into chamber 120 in the manner previously described and tubular segment 118 sealed as shown in the drawings. After the specimen has been taken by the physician and the swab reinserted serted into the apparatus in the manner shown in FIG. 15, squeezing the yieldable sidewalls of squeeze bulb or chamber 120 will cause the transport fluid to be injected into chamber 122 via passageways 124, 126, 128 and 130. Chamber 120 is of such a volume that when the fluid is transferred from chamber 120 into chamber 122, the fluid will substantially encapsulate bibulous swab material 56 which is disposed within chamber 122. With the fluid transport medium having saturated the bibulous swab material, the entire apparatus can be safely transported to the clinical laboratory for testing.

As indicated in FIGS. 16, 17 and 18, once again the plastic body portion 110 of the apparatus is shown in these drawings is substantially circular in cross section at any point. It is to be noted that fluid passageways 128 are disposed on opposite sides of chamber 122 and are carried by means of a plastic, flange-like reinforcement 132 (FIGS. 13, 15, 17 and 18).

Turning now to FIGS. 19 through 24, still another form of the apparatus of the invention is there shown. Once again, this form of the apparatus is similar in many respects to the apparatus described in the preceding paragraphs and like numbers are used in the drawings to identify like components. The apparatus here shown comprises an elongated plastic body 140 including longitudinally spaced apart first and second chambers 142 and 144. Plastic body 140 is open proximate its upper end 146 and is provided with a tubular shaped segment 148 proximate its lower extremity 150. Tubular extremity 148 has a fluid passageway 152 which enables communication between chamber 144 and atmosphere.

In the instant form of the invention, tubular section 148, the passageway of which can be sealed by crimping or heat sealing, functions to hold a second cap, or safety shield, 156 in position about the lower squeeze bulb or chamber 144. With this unique construction, when the closure cap 156 is moved from the position shown in the phantom lines in FIG. 21 into the position shown in the solid lines, tubular section 148 is closely receivable within a centrally disposed aperture 157 formed in safety shield member 156. As the member 156 is snapped into position about the lower end of the apparatus, its upstanding walls surround the squeeze bulb or chamber 144 thereby serving to positively preclude any inadvertent squeezing of the chamber and the resulting accidental injection of the transport medium into chamber 158.

In using this latter form of the apparatus safety cap 156 is removed, and the appropriate transport fluid 65 drawn into chamber 144 through open passageway 152. After the chamber has been filled and passageway 152 appropriately sealed, safety member or cap 156 is snapped in place thereby surrounding chamber 144 in the manner illustrated in the solid lines of FIG. 21.

As was the case with the earlier described embodiments of the invention, this form of the invention also includes an intermediate reduced-diameter portion shown here in the form of a third squeeze bulb or chamber 158. As best seen in FIG. 21, chamber 158 is axially off-set and is in communication with first and second chambers 142 and 144 by means of a novel circuitous fluid flow path of a character presently to be described.

Contained within the apparatus of the invention is a removable swab assembly 52 of a configuration virtually identical to that previously described. The upper extremity of swab assembly 52 is receivable within a bore formed in a cap 72 which cap is also of virtually identical construction to the cap used in connection with the previously described embodiments of the invention.

After the specimen has been taken by the physician and the swab reinserted into the apparatus in the manner shown in FIGS. 19 and 21 and with the cap member 156 closing off passageway 152, squeezing the deformable side walls of chamber 144 will cause the transport fluid 65 to be injected into axially offset chamber 158 via the circuitous fluid path now to be described. Referring to FIG. 21, this circuitous fluid flow path can be seen to comprise a first longitudinally extending fluid passageway 160 which intersects a transversely extending passageway leg 162. Passageway 162 in turn communicates with a longitudinally extending passageway 164 which communicates proximate its upper end with a short transversely extending passageway leg 166. Passageway 166 terminates at the upper portion of chamber 158. With this construction when the flexible side walls of chamber 144 are squeezed, fluid will be injected into chamber 158 via the circuitous passageway thus described following the path indicated by the arrows in FIG. 21. Once again chamber 144 is of a sufficient volume to insure that the bibulous portion of the swab 52 will be fully saturated with the transport medium prior to transport of the apparatus to the clinical laboratory for testing. As was the case with the previous described embodiments of the invention, the unique circuitous fluid flow path between chambers 144 and 158 prevents accidental transfer of the transport fluid into the swab containing chamber through vibration, shaking or rough handling of the apparatus.

As indicated in FIGS. 22, 23 and 24, plastic body 140 is of generally circular cross section at any point. Chamber 158 is also of circular cross section but is axially displaced as indicated in FIG. 22. This axially displacement permits the formation of the circuitous passageway with leg 164 of the passageway being structurally supported by the transversely extending web 167 (FIGS. 21 and 23). Lower chamber 144 is also circular in cross section at any point as is second closure cap 156.

Referring now to FIGS. 25 through 30, yet another form of the swab form apparatus of the present invention is there shown and generally designated with the numeral 170. The apparatus of this form of the invention is similar in many respects to the embodiments previously described and once again like numbers are used in the drawings to identify like components. The apparatus is used for transporting a swab 52, the stem of which is closely received within a bore formed in a closure cap 72 of a construction identical to that previously described herein.

The apparatus comprises an elongated plastic body 172 having an open end portion 174 which is closed by closure cap 72 and a lower portion 176. Body 172 includes a upper elongated flexible-walled chamber 178 and a lower flexible-walled chamber 180. Disposed intermediate chambers 178 and 180 is a reduced diameter portion provided here in the form of a third flexiblewalled chamber 182.

Disposed proximate the second end 176 of the plastic body is a tubular shaped segment 184 having a fluid passageway 186. In the drawings passageway 186 is shown in a sealed condition, segment 184 having been crimped and heat-sealed in a manner previously described. Once again, if desired, a mechanical clamping means can be used to sealably close segment 184.

Chambers 180 and 182 are in fluid communication via a circuitous fluid path comprising a longitudinally extending elongated fluid passageway 188. Passageway 188 is connected proximate its lower end with a transversely extending passageway 190 which communicates with chamber 180 proximate its lower end. Passageway 188 communicates proximate its upper or opposite end with a transversely extending passageway 192 which in turn communicates with chamber 182 proximate the upper end of this chamber.

A highly novel feature of the apparatus of the invention as shown in FIG. 27 comprises the provision of a fourth chamber 194. Fourth chamber 194 is in communication with chamber 182 via a fluid passageway comprising a longitudinally extending passageway 196 and a transversely extending passageway 198 which communicates with chamber 182 proximate its lower end. In the present form of the invention, fourth chamber 194 is provided with flexible side walls and is disposed on one side of and in close proximity with chamber 180.

As best seen by referring to FIGS. 28, 29 and 30, chambers 178, 180, 182 and 194 are all circular in cross section at any point. Passageway 188 is supported by a structural reinforcing web 200.

In using the apparatus illustrated in FIGS. 25 through 30, a fluid such as a transport medium 65, can be drawn into chamber 180 by inserting tubular segment 184 into a vial containing the fluid, squeezing the walls of flexible chamber 180 and then releasing them to cause the fluid 65 to be drawn into chamber 180 in the manner shown in FIG. 27. Once the transport medium most appropriate for use in connection with the culture to be taken is drawn into chamber 180, passageway 186 of tubular segment 184 can be heat-sealed in the manner previously described so as to assume the configuration shown in the drawings.

After the specimen has been taken by the physician and the swab reinserted into the apparatus in the manner shown in FIG. 27, squeezing the yieldable side walls of chamber 180 will cause the transport fluid to be injected into chamber 182 via passageways 188, 190 and 192. Chamber 180 is of a volume such that when the fluid is transferred from chamber 180 into chamber 182 the fluid will substantially encapsulate the bibulous swab material 56 carried by the swab 52. Once the transport fluid has been injected into chamber 182 a small portion of the culture or specimen residing on the swab material will normally be transferred to the fluid transport medium. By squeezing and then releasing the flexible side walls of chamber 194, a part of the transport fluid now contaminated with the specimen will be drawn into chamber 194 via passageways 196 and 198. By severing the length of tube 197 which interconnects chambers 182 and 194, the contaminated transport fluid contained within chamber 194 and designated in FIG. 27 by the numeral 65a can be readily separated from the apparatus. After severing tubular segment 197, chamber 194 can be sealed by heat-sealing or otherwise closing passageway 196 of tubular segment 197. Alternatively, segment 197 can first be heat sealed along a portion of its length and then cut through the sealed portion to separate chamber 194 from the device. This sealing and cutting operation can be accomplished in either one or two steps as desired. The contaminated transport fluid contained within chamber 194 can then be safely transported to the clinical laboratory for testing. This unique feature of the apparatus permits clinical testing of the contaminated transport fluid 65a as well as separate clinical analysis of the contaminated swab 52. Testing of the contaminated fluid 65a may be preliminary to testing of the swab or may allow testing of the specimen by a different method.

Turning finally to FIGS. 31 through 35, a last embodiment of the invention is thereshown. Many portions of the apparatus of this form of the invention are similar to those described in connection with the apparatus described FIGS. 13 through 15. However, the relative positioning of the various fluid chambers of the apparatus is somewhat different. The apparatus of this last form of the invention comprises an elongated plastic body portion 201 having a longitudinally extending first or upper chamber 202 and a second longitudinally spaced chamber 204. Chamber 202 is open proximate its upper end and is adatted to sealably receive a closure member or cap 72 carrying a swab assembly 52 of the character previously described. Formed proximate the lower portion 206 of body 200 is a tubular shaped segment 208 having a fluid passageway 210 through which transport fluid can be drawn to fill lower chamber 204. After chamber 204 has been filled with the selected transport fluid medium, tubular segment 208 is heat-sealed in the manner previously described and as indicated in the drawings. Segment 208 can also be sealed using a mechanical clamp if so desired.

Disposed intermediate chambers 202 and 204 is a reduced diameter portion comprising a third flexible-walled elongated chamber 212. As indicated in FIG. 33, chambers 202, 204 and 212 are all axially aligned and are in communication with one another via a novel arrangement of fluid passageways of a character presently to be described.

As best seen by referring to FIGS. 33 through 35, passageway 210 of tubular segment 208 communicates with chamber 204 via an elongated axially extending fluid passageway 214. Intersecting passageway 214 is a transversely extending passageway 216 which communicates at its outer end with an elongated, longitudinally extending passageway 218 which passageway extends on side of chambers 204 and 212. Proximate the upper extremity of passageway 218 is a transversely extending sub-passageway 220 which communicate with chamber 212 proximate its upper end. In the form of the invention shown in FIG. 33, a second, longitudinally spaced sub-passageway 222 is also provided. This passageway communicates with chamber 212 proximate the central section thereof. With this arrangement fluid flowing through passageway 218 can enter chamber 212 through sub-passageway 220 as well as through sub-passageway 222. Once again, as indicated in FIGS. 31 and 33, passageway 218 is structurally supported by a reinforcing web 224.

In using this last form of the apparatus, a fluid such as an appropriate transport medium is either prepackaged with the device or is drawn into chamber 204 in the manner previously described and tubular segments 208 is then clamped or sealed as shown in the drawing. After the specimen has been taken by the physician and the swab reinserted into the apparatus in the manner shown in FIGS. 31 and 33, squeezing the yieldable side walls of the squeeze bulb or chamber 204 will cause the transport fluid to be injected into chamber 212 via passageways 216, 218, 220 and 222. Chamber 204 is of such a volume that when the fluid is transferred into chamber 212 the fluid will substantially encapsulate the bibulous swab material 56 of swab 52 which is disposed proximate the lower extremity of chamber 212. With the fluid transport medium having saturated the bibulous swab material, the entire apparatus can be safely transported to the clinical laboratory for testing.

As indicated in FIGS. 34 and 35, once again plastic body 200 of the apparatus is substantially circular in cross section at any point as are chambers 204 and 212.

A particular advantage of this last to be described embodiment of the invention resides in the placement of chambers 212 and 204 and there interconnection through the novel circuitous flow path defined by passageways 214, 216, 218, 220 and 222. The location of chambers 204 and 212, coupled with the configuration of the circuitous flow path, positively precludes accidental transfer of the fluid medium from chamber 204 into 212 as a result of handling, shock or vibration of the apparatus of the invention. For example, even through violent shaking of the apparatus of this last form of the invention, the fluid in chamber 204 cannot reach chamber 212. Rather, the transfer of fluid can be accomplished only by positive manipulation of the flexible outer walls of chambers 204 and 212.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A swab transport apparatus for containing and transporting a swab of the character having an elongated stem and a bibulous swab material carried proximate one end of the stem, said apparatus comprising:
   (a) an elongated longitudinally extending plastic body having first and second ends, said body being open at said first end and including:
      (i) a first elongated chamber having resiliently deformable side walls communicating with said first open end for receiving at least a portion of the swab;
      (ii) a second chamber having resiliently, deformable side walls for containing fluid therewithin, said second fluid medium chamber being longitudinally spaced from said first chamber;
      (iii) a third chamber having resiliently deformably side walls disposed intermediate said first and second chambers, said third chamber being in communication with said first chamber via an axially extending fluid passageway and said third chamber being in communication with said second chamber via a circuitous fluid flow path; and
      (iv) a tubular segment formed proximate said second end of said body having a fluid passageway extending therethrough for interconnecting said second chamber with atmosphere;
   (b) a removable first cover means for sealably closing said open first end of said tube, said first cover means including an axially extending bore for closely receiving a portion of the elongated stem of the swab; and
   (c) a removable second cover means carried by said tubular segment for surrounding said second chamber to prevent inadvertent deformation of the side walls thereof.

2. A swab transport apparatus as defined in claim 1 in which said second cover means comprises a cup shaped member having curved outer walls and an aperture formed in said walls for closely receiving said tubular segment.

3. A swab transport apparatus as defined in claim 1 in which said first and second chambers are axially aligned and in which said third chamber is axially offset with respect to said first and second chamber.

4. A swab transport apparatus as defined in claim 3 in which a portion of said circuitous fluid flow path extends parallel to a longitudinal axis of said third chamber and a portion of said circuitous fluid flow path extends perpendicular to the axis of said third chamber.

* * * * *